US005887585A

United States Patent [19]

Dusenbery

[11] Patent Number: 5,887,585

[45] Date of Patent: Mar. 30, 1999

[54] AIR SUPPLY LIFE VEST

[76] Inventor: Matthew Lee Dusenbery, 3600 Elizabeth Ave. SE. #19-101, Olympia, Wash. 98501

[21] Appl. No.: 905,675

[22] Filed: Aug. 4, 1997

[51] Int. Cl.$^{6}$ .................................................. A61M 15/00

[52] U.S. Cl. .............................. 128/202.14; 128/201.27; 128/205.22

[58] Field of Search ........................ 128/201.27, 201.28, 128/202.14, 205.22, 202.19; 405/186; 441/106; 114/315; 224/148.7, 628

[56] References Cited

U.S. PATENT DOCUMENTS

| | | | |
|---|---|---|---|
| 1,878,474 | 9/1932 | Dräger et al. . | |
| 2,982,105 | 5/1961 | Akers | 128/205.22 |
| 3,135,098 | 6/1964 | Root | 128/205.22 |
| 3,536,071 | 10/1970 | Ferrando . | |
| 3,820,348 | 6/1974 | Fast . | |
| 4,054,132 | 10/1977 | Deeds | 128/202.14 |
| 4,227,521 | 10/1980 | Hart et al. . | |
| 4,383,528 | 5/1983 | Eppolito | 128/205.22 |
| 4,438,764 | 3/1984 | Eppolito | 128/205.22 |
| 4,640,215 | 2/1987 | Purifoy, Jr. | 114/315 |
| 4,739,913 | 4/1988 | Moore | 128/205.22 |
| 4,752,263 | 6/1988 | Pritchard et al. | 128/202.14 |
| 4,779,554 | 10/1988 | Courtney . | |
| 4,791,921 | 12/1988 | Robison | 128/201.27 |
| 4,964,405 | 10/1990 | Arnoth | 128/205.17 |
| 5,259,372 | 11/1993 | Gross et al. | 128/200.24 |
| 5,370,113 | 12/1994 | Parsons | 128/205.22 |
| 5,400,934 | 3/1995 | Dueros | 128/205.22 |
| 5,516,233 | 5/1996 | Courtney . | |

*Primary Examiner*—Aaron J. Lewis

*Attorney, Agent, or Firm*—Brian J. Coyne

[57] ABSTRACT

A life safety vest for white water rafting, canoeing and kayaking, with scuba air breathing apparatus. A life safety vest of the conventional kind worn about the torso, having front and rear panels that incorporate sections of flotation material, is modified by creating recesses in the flotation sections of the rear panel to receive and store miniature scuba compressed air tanks. Left and right breast pockets are provided on the front panels for storing a scuba mouthpiece and demand regulator. A flexible air hose has one end attached to the mouthpiece and demand regulator and an opposite end attached to a T-coupling. The T-coupling is also attached by hollow tubing to each of the scuba air tanks. A rigid safety cover is provided to cover the upper portion of each tank, including an air regulator mounted atop each tank, which secures the breathing apparatus from damage due to mechanical stresses and shocks in the event of a white water boating accident.

9 Claims, 4 Drawing Sheets

AIR SUPPLY LIFE VEST

BACKGROUND OF THE INVENTION

1. Field of the Invention

The present invention relates generally to water safety gear, particularly life vests equipped with breathing apparatus.

2. Background Art

Participants in white water rafting, canoeing or kayaking face the risk of capsizing or being thrown overboard into rapid, turbulent water, sometimes followed by severe buffeting against rocks and logs, thereby incurring bodily injuries and even drowning. Prior to my invention, the principal safeguard against such dangers has been a buoyant, safety life vest worn about the torso of each participant. The life vest ordinarily provided sufficient flotation to maintain the nose and mouth of an overboard participant above water until he could be rescued. It was wholly inadequate, however, whenever he become trapped underwater—underneath a log jam or in an overturned kayak, for example—in which event he could be drowned before rescuers could find him and bring him up for air. What is required to safeguard against such a mishap in addition to a life vest is a rapidly deployable air supply for breathing underwater long enough for a rescue operation to be completed. Such an air supply apparatus, which according to the present invention comprises one or more compressed air tanks with associated regulator valves and air tubing, should be capable of withstanding the significant stresses and impulse forces to which it may be subjected in a white water environment.

Drager et al., U.S. Pat. No. 1,878,474, disclosed an annular, hollow breathing bag made of a water-proof elastic or flexible material and constructed to fit snugly against the shoulders, back and chest of the wearer. A breathing hose having one end connected to a sodium peroxide cartridge inside the bag, and an opposite end connected to a mouthpeice, conducted exhaled breath to the bag and inhaled, oxygen-laden air to the wearer's mouth. This arrangement, intended for occupants of sunken submarine boats or diving bells, was unsuitable for whitewater conditions as it provided inadequate buoyancy and left the cartridge subject to damage by impact with rocks and other objects.

Courtney, U.S. Pat. No. 5,516,233, disclosed a vest style bouyancy compensator adapted to carry a rescue raft and to be worn by a diver carrying a standard scuba tank. No provision was made for protecting the tank and associated regulator valve from damage in white water conditions.

Fast, U.S. Pat. No. 3,820,348, disclosed a back pack assembly for a diver for use with a compressed air scuba tank and equipped with flexible bladders that automatically inflated at greater depths and disinflated at lesser depths. The back pack included a two-peice housing fitted together to encompass the scuba tank. Although the back pack could provide some protection from damage to the tank and attached regulator valve, the assembly was unnecessarily complex and bulky for white water conditions.

Courtney, U.S. Pat. No. 4,779,554, disclosed a back pack, for use with an inflatable air vest, having a rigid housing that enclosed a compressed air tank, and equipped with an inflatable buoyancy compensator for use in deep sea diving. This too was unnecessarily complex and bulky for white water conditions.

Hart, U.S. Pat. No. 4,227,521, disclosed an air system for scuba diving that included an inflatable buoyancy jacket and scuba breathing gear, including a compressed air tank. In an emergency, the compressed air tank could be jettisoned, and the diver could breathe the air in the inflated jacket through a mouthpeice. No provision was made for protecting the scuba breathing gear from damage in white water conditions.

There remains a need, therefore, for an air supply vest that will provide both adequate buoyancy and a rapidly deployable supply of air to a boating accident victim, wherein the air supply is secure from mechanical damage under white water conditions.

SUMMARY OF THE INVENTION

It is therefore an object of the invention to provide a buoyant life vest equipped with a rapidly deployable air supply apparatus for use in white water rafting, canoeing and kayaking.

It is a further object of the invention to provide such a life vest wherein the air supply apparatus is secure from mechanical damage in the event the wearer falls or is thrown into the water.

A still further object of the invention is to provide such a life vest that is compact and comfortable for a boating participant to wear about his torso.

Other objects of the invention include providing such a life vest that is simple in construction and incorporates readily available scuba air breathing gear.

Accordingly, the present invention provides a flotation life vest of generally conventional construction, including one or more layers of flotation material, but modified to house and incorporate scuba air breathing apparatus. The vest has front and rear portions, the rear portion having at least one recess—preferably two parallel recesses—for receiving and storing a miniature compressed air storage tank equipped with a top-mounted regulator valve assembly, and the front portion having at least one pocket for receiving and storing a scuba mouthpeice regulator. Each such pocket preferably is lined for low surface friction in order to facilitate easy and rapid removal of the mouthpeice regulator in an emergency. Attached to the vest is means for connecting the mouthpeice regulator to at least one miniature compressed air tank through the regulator valve attached to said tank. A rigid safety cover is provided for each tank, which cover has a hollow core, open at one end, for placement over the valve assembly and upper portion of each tank, thereby protecting the valve assembly from damage from mechanical shocks and stresses. In a preferred embodiment, each core is made from carbon fiber and has a non-slip lining. Inasmuch as miniature scuba air tanks come in standard short and long lengths, inserts made from flotation material and adapted to fill in a lower portion of each tank storage recess are provided for use with the short version miniature tank.

The terms "left" and "right" will be understood to refer to the orientation of the various aspects of the air supply vest as they would be referred to by a person wearing said vest.

DETAILED DESCRIPTION OF THE ILLUSTRATED EMBODIMENT

Figure 1:
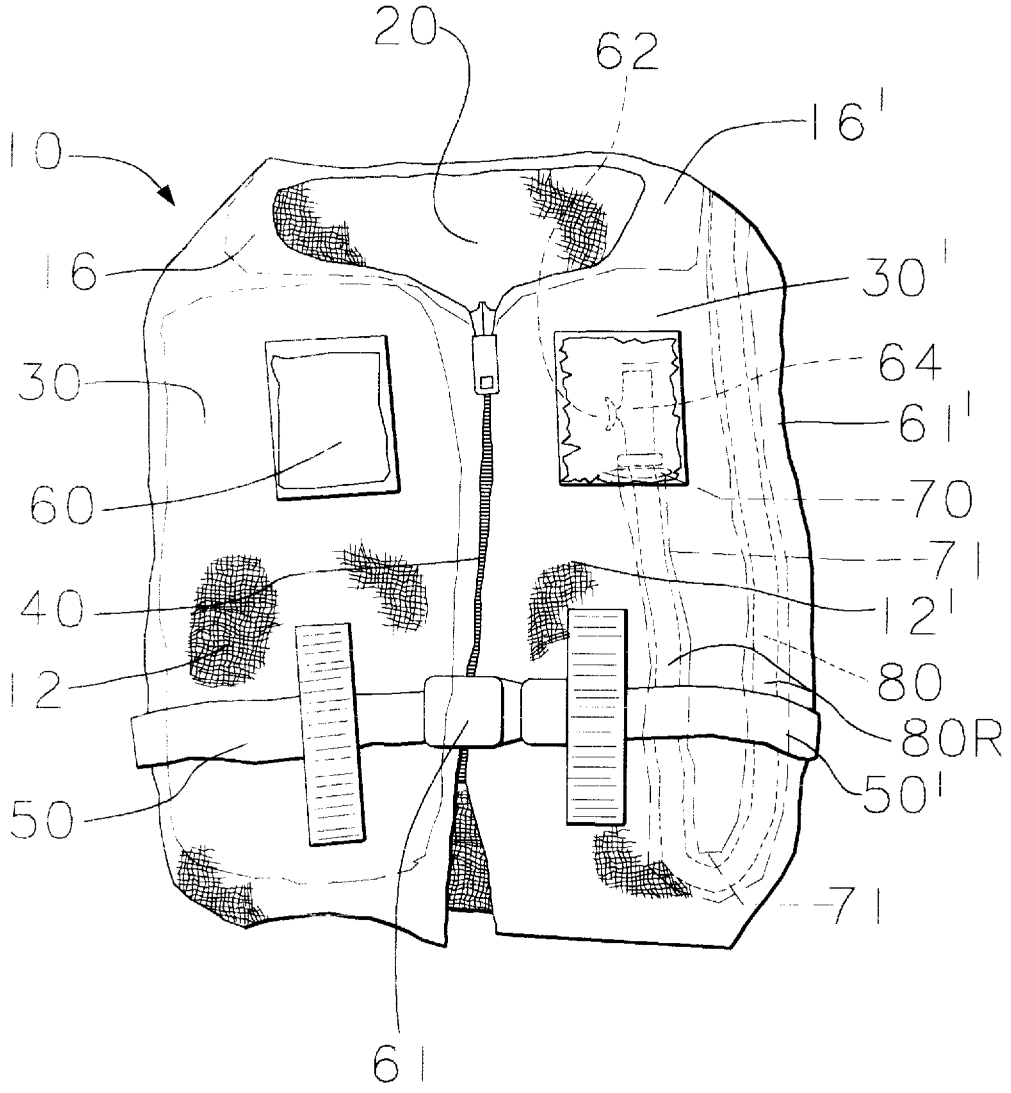
FIG. 1 is a front, elevational view of a preferred embodiment of my air supply vest, showing in dotted outline a mouthpeice and regulator body inside a left breast pocket thereof and attached flexible air hose.
Figure 2:
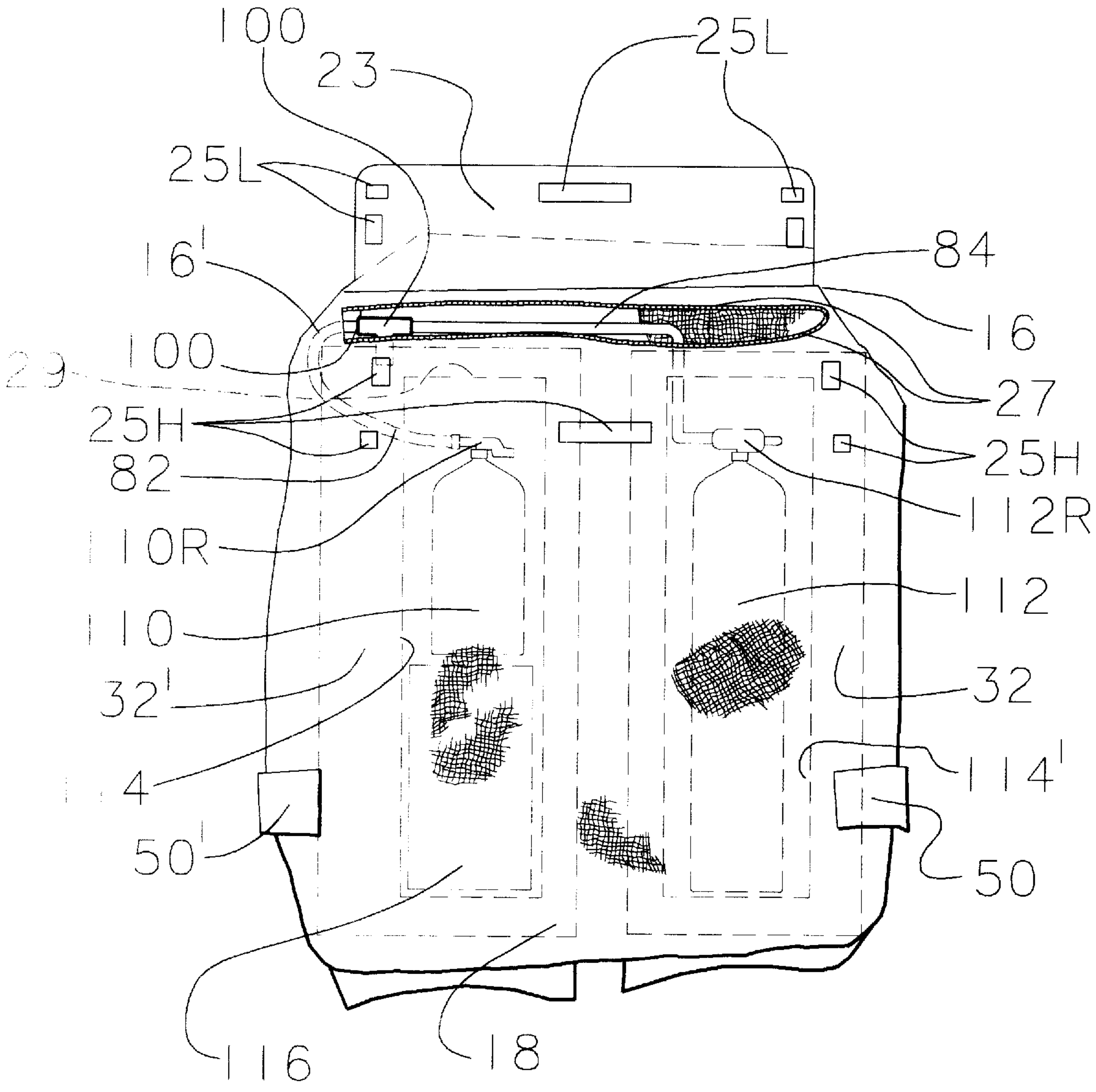
FIG. 2 is a rear elevational view thereof with the rear flap raised and the tank access opening unzippered, showing left and right flotation sections in dashed outline, and in dotted outline a recess cutout in each flotation section and miniature scuba air tank housed therein.
Figure 3:
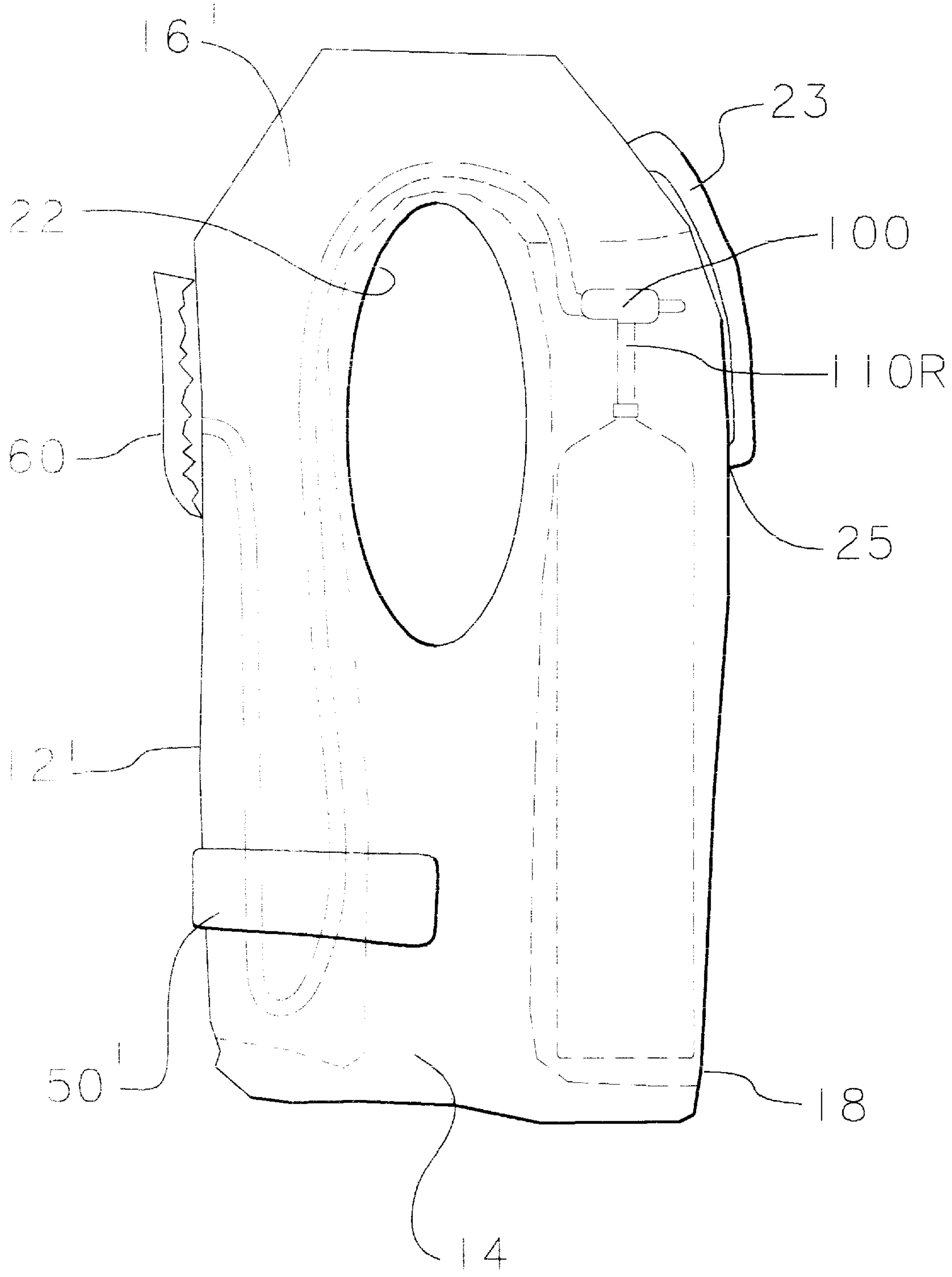
FIG. 3 is an elevational view of the left side thereof with the rear flap lowered and secured, showing in dashed outline front and rear flotation sections and in dotted outline the mouthpiece, regulator body, flexible air hose and miniature air tank.

FIGS. 1–3 depict my air supply vest, denoted generally by the numeral 10, which is a personal flotation device of conventional construction that has been modified to house scuba air breathing apparatus. The vest 10 includes front portions, comprising right and left front panels 12, 12', joined by side panels 14 and by right and left shoulder panels 16, 16' to a rear panel 18, thereby defining a neck opening 20. The shoulder panels 16, 16' and the side panels 14 are of nylon, and the side panels 14 have arm cutouts 22. The front panels 12, 12' and rear panel 18 comprise flotation material, such as AQUAFOAM® (a trademark of Stearns Manufacturing Company of St. Cloud, Minn.), encased between inner and outer layers of nylon. In the particular embodiment illustrated, the right and left front panels 12, 12' each contain a single section of flotation material 30, 30', and the rear panel 18 likewise includes adjacent right and left flotation sections 32, 32', encased between inner and outer layers of nylon. A first zipper 40 is sewn to the vertical, free margins of the front panels 12, 12'. Right and left adjustable side straps 50, 50' each have one end attached to a side panel 14 and an opposite end attached to a buckle 61.

A breast pocket 60, preferably of gathered and stiched elastic fabric, is attached to an upper, exterior surface of each front panel 12, 12', and is of sufficient size to store and retain a scuba mouthpeice 62 and regulator 64, as shown, for example, in FIGS. 1 and 2. Referring to FIGS. 1–3, a flexible air hose 80, having a first end attached to the regulator 64, passes through an aperture 70 within pocket 60 from whence, through channel 71 communicating with aperture 70 and cut in the flotation material 30', it descends, doubles back on itself, and then ascends up and around left shoulder panel 16', from whence an opposite end of the hose 80 is attached to a T-coupling 100. A portion of the flexible air hose 80 nearest the regulator 64 is left slack and forms a wide loop 80R within a lower left panel 12' in order to permit sliding the hose 80 upward and extending the mouthpeice outward from the vest 10 in the event of a white water emergency. The channel 71 is cut wider in the vicinity of the loop 80R to facillitate sliding movement of the hose 80. A first air line 82, e.g., reinforced rubber tubing, descends from the T-coupling 100 to connect to a first, miniature scuba compressed air tank 110 through air regulator 110R mounted atop said tank.

As shown in FIG. 2, the tank 110 is installed through a horizontal tank access opening 29 that extends between the shoulder regions of the jacket and into a vertically-extended recess 114' in left, rear flotation section 32'. Tank 110 is a short version tank; that is, the height of tank 110 is only eight inches, more or less.

Extending rightwards from the T-coupling 100 is a second air line 84 that connects to a second miniature scuba compressed air tank 112 through air regulator 112R mounted atop said tank. Tank 112 is a long version miniature tank, that is, the height of tank 112 is twelve inches, more or less, and it is installed into vertically-extended recess 114 in the right rear flotation section 32. The recesses 114, 114' are substantially equal in size. Therefore, whenever the short version tank 112 is used, a flotation section insert 116, of suitable dimensions to fill a lower portion of recess 114' underneath the tank 112, is positioned therein.

The upper and lower margins of the tank access opening 29 are lined with a second zipper 27. A horizontally-elongated, substantially rectangular, rear flap 23 is attached to the shoulder panels 16, 16' above and parallel to the second zipper 27, and patches of loop material 25L of a hook and loop fasteners, e.g., VELCRO®, are attached to an undersurface 23U thereof. Mating hook patches 25H of a hook and loop fastener are attached to corresponding areas of the shoulder panels 16, 16'.

Figure 4:
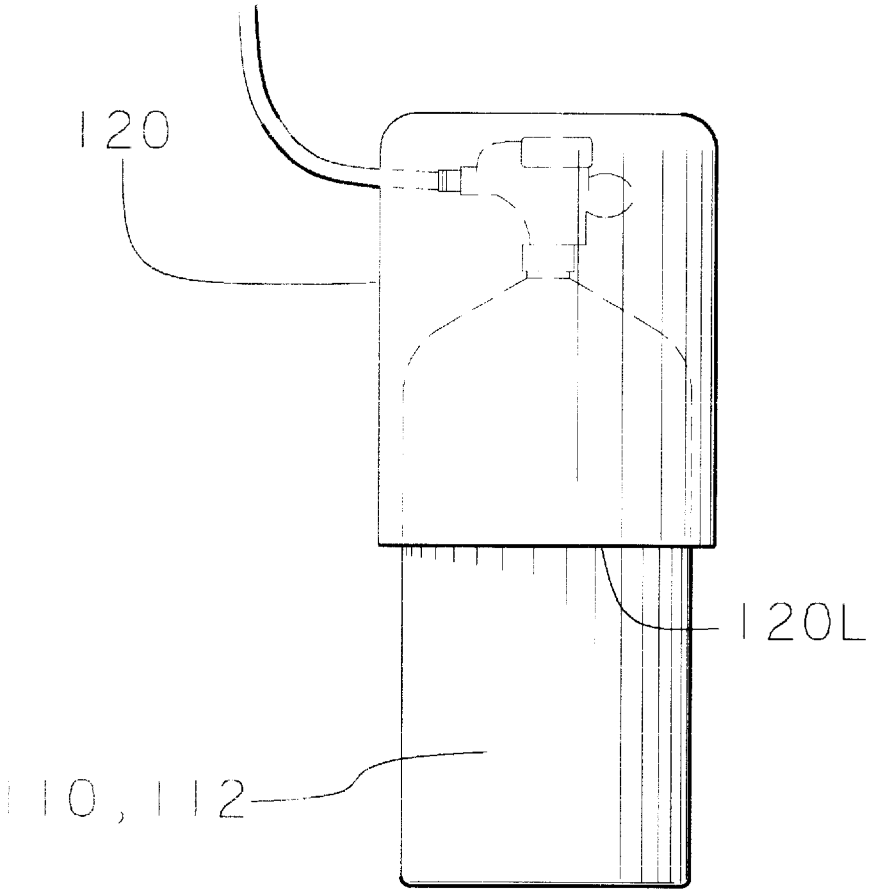
FIG. 4 is an enlarged, rear elevational view of a miniature air tank with a cylindrical safety cover in place over the regulator valve.
Figure 5:
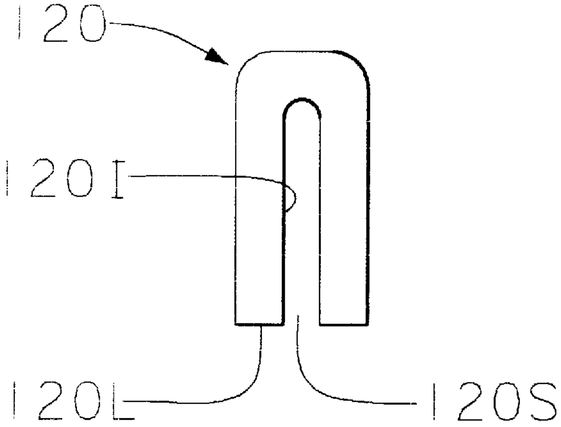
FIG. 5 is a left side elevational view of the cover showing a slot for attachment of the air hose to an air regulator mounted atop the tank.
Figure 1:
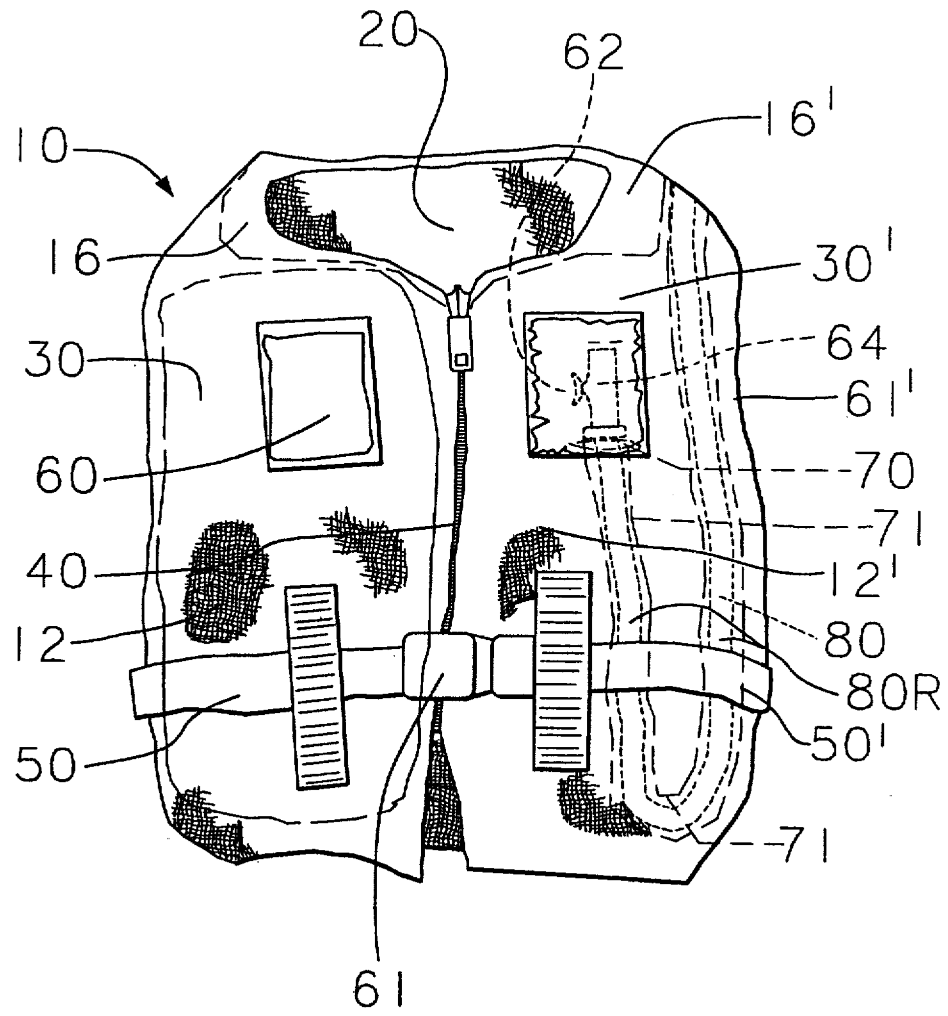
Figure 2:
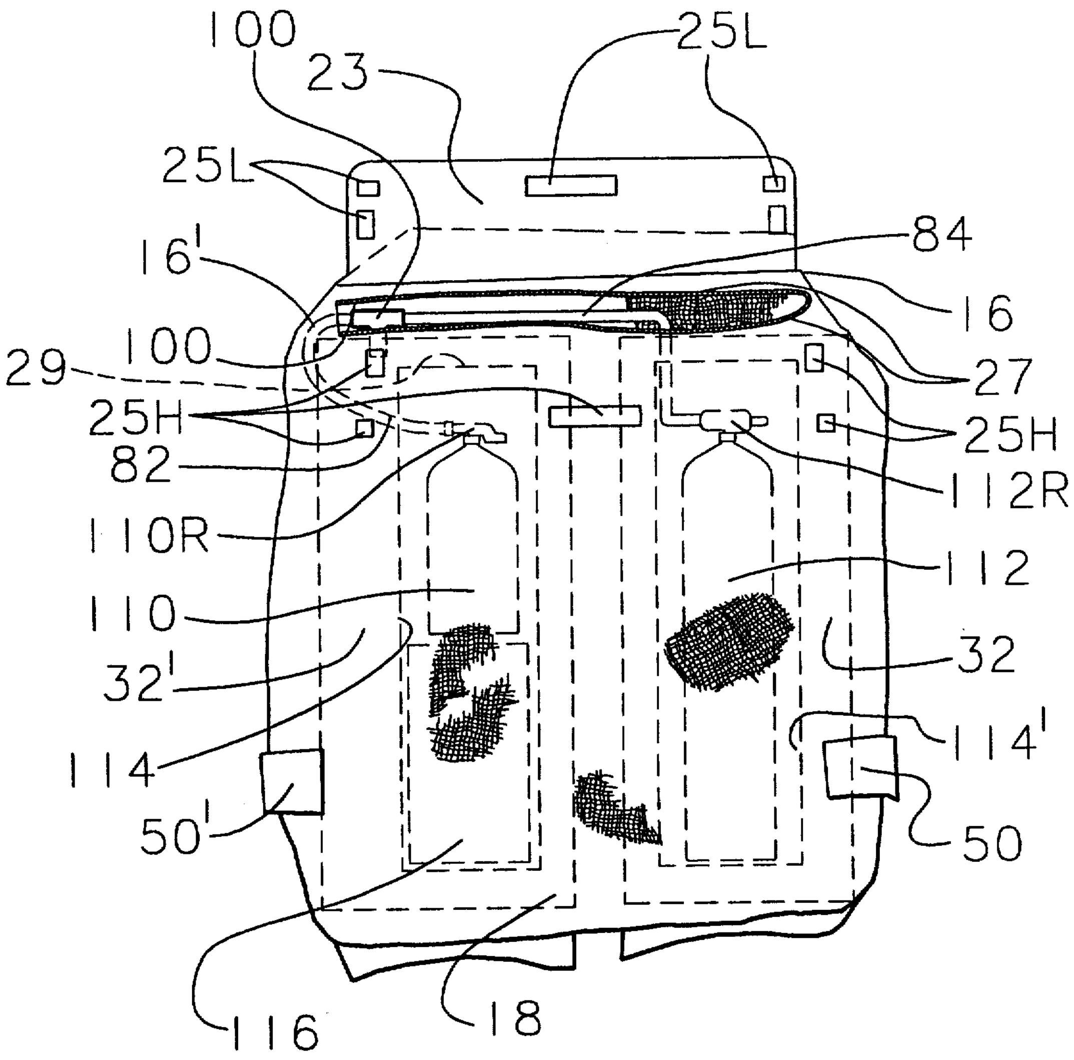
Figure 3:
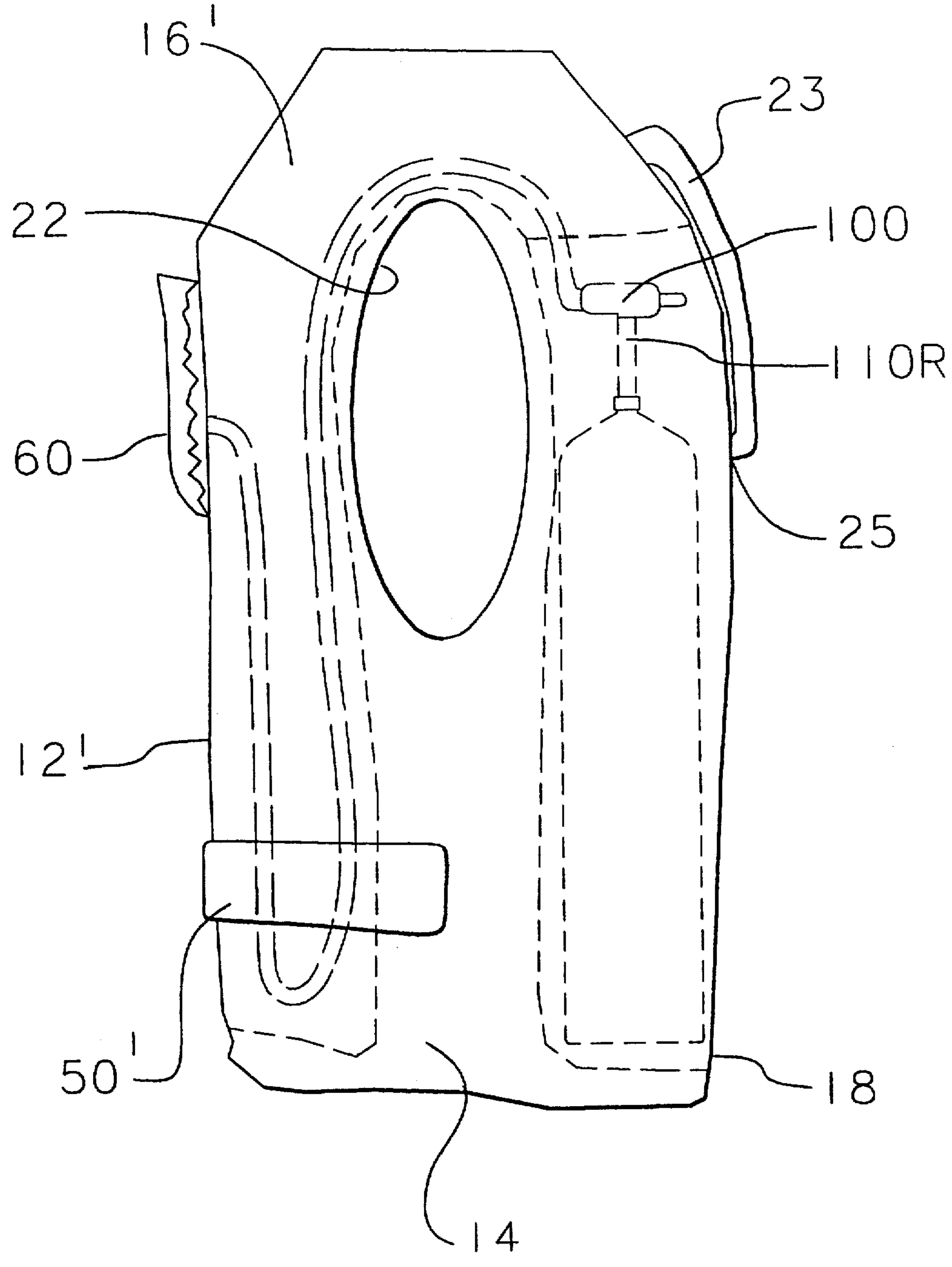
Figure 4:
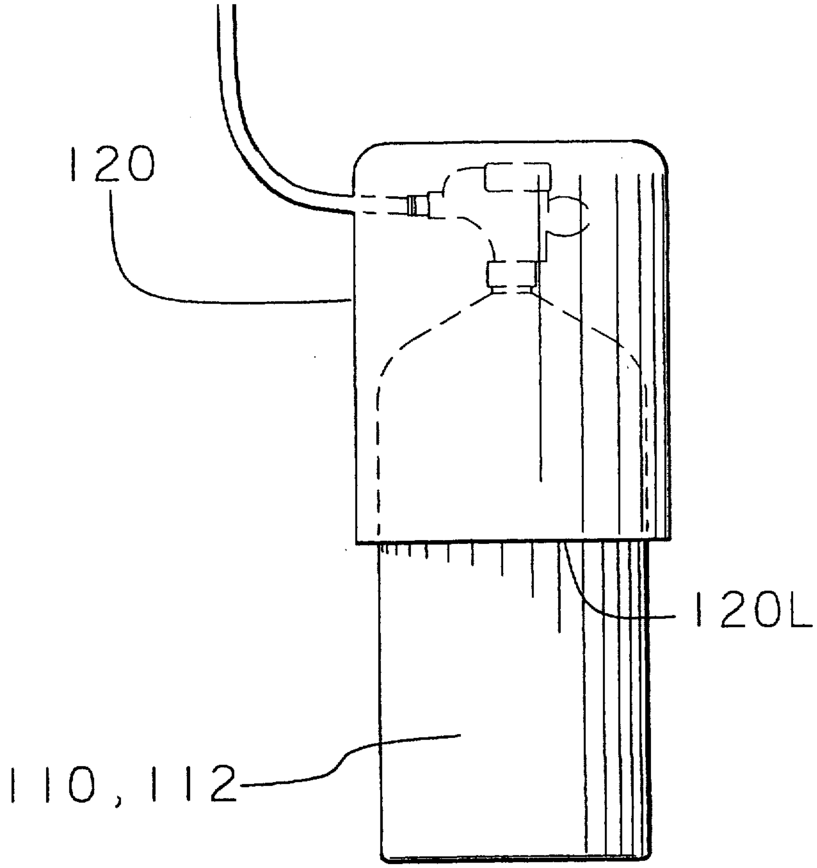
Figure 5:
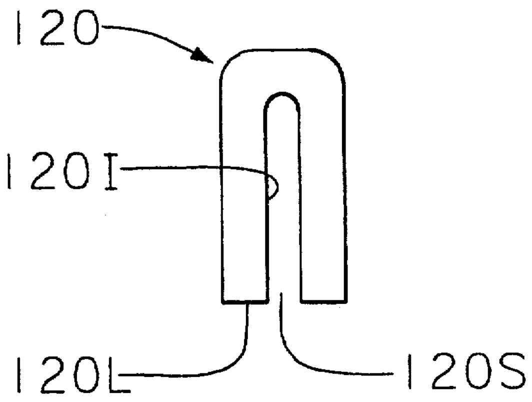

In a preferred embodiment, the upper portions of the tanks 110, 112 and the tank regulators 110R, 112R are each provided with a rigid safety cover 120 having a hollow core, closed across a top end and open at a lower end, as shown in FIGS. 4 and 5, which extends part way down the tank 110, 112. Each cover has a vertical slot 120S that extends from a lower margin 120L thereof part way up the cover, which permits access through the cover 120 for connection of an air line 82, 84 to an air tank 110, 112. Each cover 120 is preferably made of carbon fiber and has a non-slip lining on the interior surface 120I thereof to minimize the risk of the cover being dislodged from the tank 110, 112 and regulator 110R, 112R. The hose 80 and air lines 82, 84 are preferably of plastic, and pressure rated at 350 p.s.i.

In the event of a water-related accident requiring an emergency supply of air, or even in the event of a military rescue of life-vested personnel at sea, the wearer of the vest 10 grasps with one hand the mouthpeice 62 and pulls it out of the pocket 60 toward and into his mouth, pulling the flexible air hose 80 outward through channel 71 as he does so. To facilitate this, each breast pocket 60, 60' is preferably lined with a low-friction lining. Although in the illustrated embodiment the mouthpeice and demand regulator are shown stored in the left pocket 60', which would be appropriate for a right-handed person, a left-handed person would instead store the mouthpeice and demand regulator in the right pocket 60.

It will be appreciated that modifications can be made to the exact form of the present invention without departing from the scope thereof. It is accordingly intended that the disclosure be taken as illustrative only and not limiting in scope, and that the scope of the invention be defined by the following claims.

I claim:

1. An air supply life vest, comprising:

a flotation life vest having front and rear portions containing flotation material encased between inner and outer layers of fabric, the rear portion having at least one recess in the flotation material therein for receiving and storing a miniature compressed air storage tank equipped with a top-mounted air valve assembly, and the front portion having at least one recess for receiving and storing a mouthpiece regulator;

at least one miniature compressed air storage tank;

a mouthpiece regulator;

means attached to the vest for connecting the mouthpiece regulator to at least one tank; and tank access opening means attached to a rear portion of the vest.

2. The air supply life vest of claim 1, further comprising at least one rigid safety cover having a hollow core, open at one end, for placement over the valve assembly and upper portion of each tank, thereby protecting the valve assembly from damage due to mechanical shocks and stresses.

3. The air supply vest of claim 2, wherein each cover is made from carbon fiber.

4. The air supply vest of claim 3, wherein the hollow core has a non-slip lining.

5. The air supply vest of claim 2, wherein the rear portion of the vest has two parallel recesses, the vest is equipped with two tanks for insertion and storage in said parallel recesses, and the means attached to the vest for connecting the mouthpiece regulator to the tanks comprises:

a T-coupling;

air tubing connecting the mouthpiece regulator to the T-coupling; and additional air tubing connecting the valve assembly for each of the tanks to the T-coupling.

6. The air supply vest of claim 5, wherein the outer layer of an upper rear portion of the vest has a horizontal slit defining upper and lower margins thereof, and the tank access opening means comprises:

a zipper attached to the upper and lower margins of the slit; and a rear flap attached to said upper rear portion of the vest above said zipper, which flap is moveable from a secured, lower position overlying said zipper to a raised position to permit insertion or removal of a tank.

7. The air supply vest of claim 6, wherein the front portion of the vest includes a left pocket and a right pocket for insertion and storage of the mouthpiece regulator, depending upon whether the vest is to be used by a right-handed or a left-handed person, respectively.

8. The air supply vest of claim 7, wherein the interior surfaces of the left pocket and right pocket are lined for low surface friction in order to facillitate easy and rapid withdrawal of the mouthpeice regulator in an emergency.

9. The air supply vest of claim 3, 4, 5, 6 or 7, further comprising a pair of elongated inserts formed from flotation material, having a length about one-half the length of each of the parallel recesses, for insertion into a bottom portion of said recesses whenever it is desired to install into the vest tanks that are shorter than the length of said recesses.

* * * * *

UNITED STATES PATENT AND TRADEMARK OFFICE

CERTIFICATE OF CORRECTION

PATENT NO. : 5,887,585
DATED : Mar. 30, 1999
INVENTOR(S) : Dusenbery

It is certified that error appears in the above-identified patent and that said Letters Patent is hereby corrected as shown below:

The title page should be deleted to appear as per attached title page.

Please delete drawing sheets 1-4 and substitute drawing sheets 1-4 as per attached.

Signed and Sealed this

Twenty-ninth Day of June, 1999

Attest:

Q. TODD DICKINSON

*Attesting Officer*

*Acting Commissioner of Patents and Trademarks*

United States Patent [19]

Dusenbery

[11] Patent Number: 5,887,585

[45] Date of Patent: Mar. 30, 1999

[54] AIR SUPPLY LIFE VEST

[76] Inventor: Matthew Lee Dusenbery, 12003 228th Street, NE, Arlington, Washington, 98223

[21] Appl. No.: 905,675

[22] Filed: Aug. 4, 1997

[51] Int. Cl.[6] .................................................. A61M 15/00

[52] U.S. Cl. ............................. 128/202.14; 128/201.27; 128/205.22

[58] Field of Search ........................ 128/201.27, 201.28, 128/202.14, 205.22, 202.19; 405/186; 441/106; 114/315; 224/148.7, 628

[56] References Cited

U.S. PATENT DOCUMENTS

| | | | |
|---|---|---|---|
| 1,878,474 | 9/1932 | Dräger et al. . | |
| 2,982,105 | 5/1961 | Akers | 128/205.22 |
| 3,135,098 | 6/1964 | Root | 128/205.22 |
| 3,536,071 | 10/1970 | Ferrando . | |
| 3,820,348 | 6/1974 | Fast . | |
| 4,054,132 | 10/1977 | Deeds | 128/202.14 |
| 4,227,521 | 10/1980 | Hart et al. . | |
| 4,383,528 | 5/1983 | Eppolito | 128/205.22 |
| 4,438,764 | 3/1984 | Eppolito | 128/205.22 |
| 4,640,215 | 2/1987 | Purifoy, Jr. | 114/315 |
| 4,739,913 | 4/1988 | Moore | 128/205.22 |
| 4,752,263 | 6/1988 | Pritchard et al. | 128/202.14 |
| 4,779,554 | 10/1988 | Courtney . | |
| 4,791,921 | 12/1988 | Robison | 128/201.27 |
| 4,964,405 | 10/1990 | Arnoth | 128/205.17 |
| 5,259,372 | 11/1993 | Gross et al. | 128/200.24 |
| 5,370,113 | 12/1994 | Parsons | 128/205.22 |
| 5,400,934 | 3/1995 | Dueros | 128/205.22 |
| 5,516,233 | 5/1996 | Courtney . | |

*Primary Examiner*—Aaron J. Lewis
*Attorney, Agent, or Firm*—Brian J. Coyne

[57] ABSTRACT

A life safety vest for white water rafting, canoeing and kayaking, with scuba air breathing apparatus. A life safety vest of the conventional kind worn about the torso, having front and rear panels that incorporate sections of flotation material, is modified by creating recesses in the flotation sections of the rear panel to receive and store miniature scuba compressed air tanks. Left and right breast pockets are provided on the front panels for storing a scuba mouthpiece and demand regulator. A flexible air hose has one end attached to the mouthpiece and demand regulator and an opposite end attached to a T-coupling. The T-coupling is also attached by hollow tubing to each of the scuba air tanks. A rigid safety cover is provided to cover the upper portion of each tank, including an air regulator mounted atop each tank, which secures the breathing apparatus from damage due to mechanical stresses and shocks in the event of a white water boating accident.

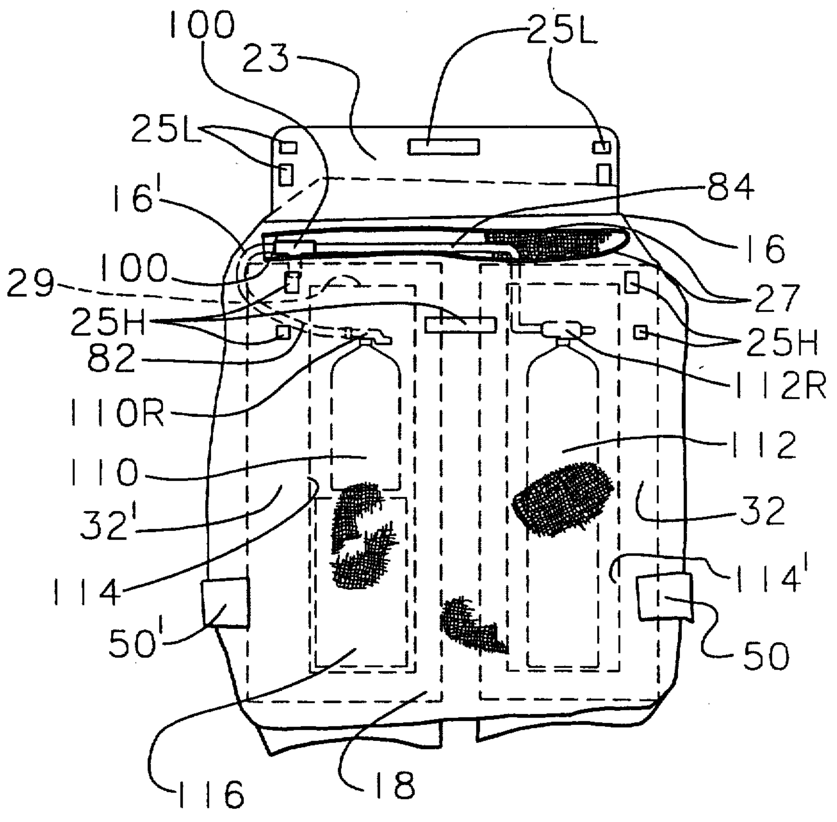

9 Claims, 4 Drawing Sheets